United States Patent
Chow et al.

(10) Patent No.: US 7,267,650 B2
(45) Date of Patent: Sep. 11, 2007

(54) ULTRASOUND DIRECTED GUIDING CATHETER SYSTEM AND METHOD

(75) Inventors: Mina Chow, Campbell, CA (US); William E. Webler, Escondido, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 532 days.

(21) Appl. No.: 10/320,728

(22) Filed: Dec. 16, 2002

(65) Prior Publication Data

US 2004/0116809 A1    Jun. 17, 2004

(51) Int. Cl.
*A61B 8/12*    (2006.01)
(52) U.S. Cl. ..................................... 600/467
(58) Field of Classification Search ............... 600/407, 600/433, 434–472, 585, 129, 139, 143, 145–6; 604/93.01, 264, 523, 95.04, 95.05, 105–108; 356/336; 73/861.29
See application file for complete search history.

(56) References Cited

U.S. PATENT DOCUMENTS

| | | | |
|---|---|---|---|
| 4,462,408 A * | 7/1984 | Silverstein et al. | ......... 600/146 |
| 4,733,669 A * | 3/1988 | Segal | .......................... 600/585 |
| 4,856,529 A * | 8/1989 | Segal | .......................... 600/454 |
| 5,058,595 A | 10/1991 | Kern | |
| 5,078,148 A * | 1/1992 | Nassi et al. | ................. 600/455 |
| 5,144,955 A | 9/1992 | O'Hara | |
| 5,190,045 A | 3/1993 | Frazin | |
| 5,190,046 A * | 3/1993 | Shturman | ................... 600/463 |
| 5,220,924 A | 6/1993 | Frazin | |
| 5,345,940 A | 9/1994 | Seward et al. | |
| 6,132,379 A | 10/2000 | Patacsil et al. | |
| 6,162,179 A * | 12/2000 | Moore | ......................... 600/466 |
| 6,167,765 B1 | 1/2001 | Weitzel | |
| 6,277,077 B1 | 8/2001 | Brisken et al. | |
| 6,306,097 B1 | 10/2001 | Park et al. | |
| 6,704,590 B2 * | 3/2004 | Haldeman | ................... 600/407 |
| 2004/0176688 A1 * | 9/2004 | Haldeman | ................... 600/443 |

* cited by examiner

Primary Examiner—Francis J. Jaworski
(74) Attorney, Agent, or Firm—Hollingsworth & Funk, LLC

(57) ABSTRACT

A guiding catheter system employs a flexible shaft having a preformed bend at a distal end. An ultrasound transducer is mounted proximal to the pre-formed bend. The ultrasound transducer has a field of view directed to a distal tip of the guiding catheter. The guiding catheter includes an open lumen adapted for the introduction of payloads through the catheter system. The guiding catheter system can be used to direct a smaller guiding catheter or guide wire into a destination vessel from a heart chamber. In one application, the guiding catheter system is used to introduce a guiding catheter into the coronary sinus ostium from the right atrium.

22 Claims, 6 Drawing Sheets

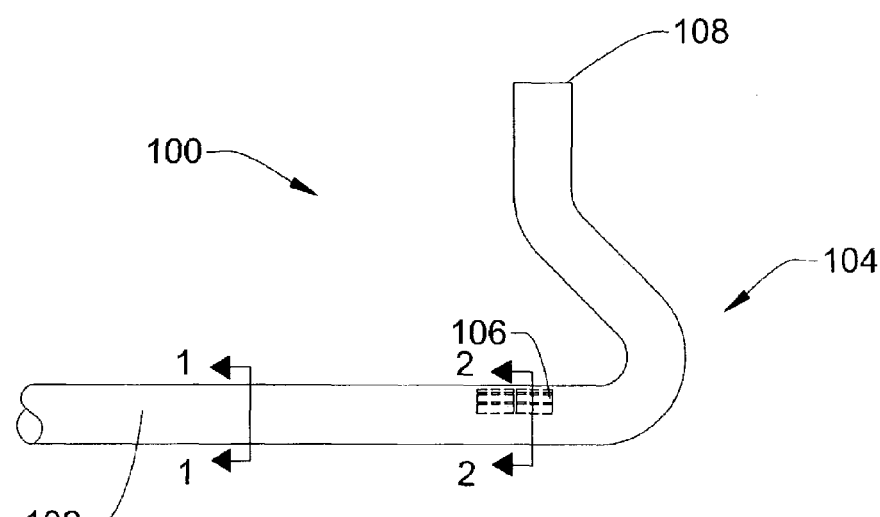
Fig. 2
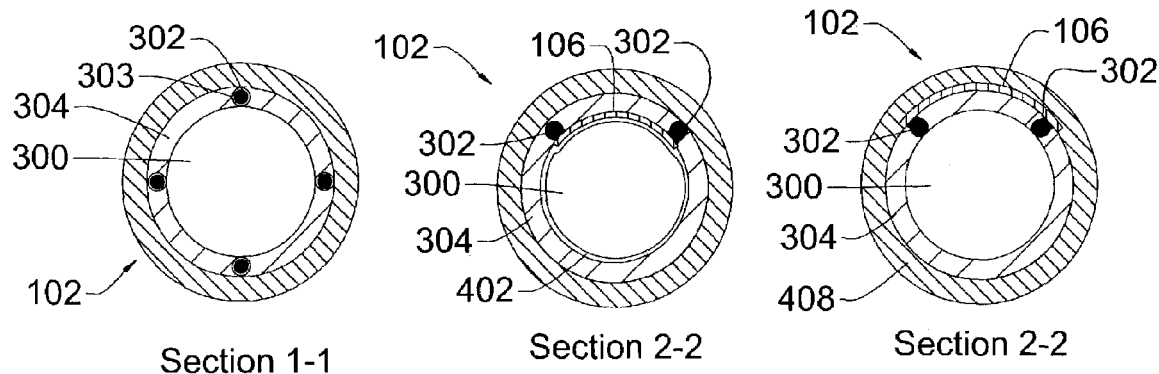
Section 1-1
Fig. 3
Section 2-2
Fig. 4A
Section 2-2
Fig. 4B Section 3-3

Section 3-3

ULTRASOUND DIRECTED GUIDING CATHETER SYSTEM AND METHOD

FIELD OF THE INVENTION

The invention relates generally to guiding catheter systems, and, more particularly, to ultrasound directed guiding catheters for accessing the coronary sinus from the right atrium.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through convoluted vasculature into a heart chamber, and then into a destination heart vessel. Once the destination heart vessel is reached, the catheter acts as a conduit for insertion of payloads into the vessel.

A pre-shaped guiding catheter is typically used to locate the destination vessel. A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. In many applications, however, the simple and familiar pre-shaped catheter makes it the preferred tool of choice.

The major goal of a guiding catheter procedure is to find and cannulate a vessel of interest in the least amount of time. Finding and cannulating the coronary sinus, for example, can become a time consuming, trial and error procedure even in a healthy patient. Patients exhibiting symptoms of advanced heart disease can have blockages or deformations of heart structure, further complicating the task of locating the ostium.

Some common techniques are used to aid the physician in visualizing the distal end of a guiding catheter during cannulation. These techniques include the procedures of angiography and venography. The procedures involve injecting a radio-opaque dye into the bloodstream to X-ray map blood vessels. Typically, the catheter is radio-opaque as well in order to be clearly located. Although effective, this method requires exposing the patient to radiation, and therefore exposure times are necessarily limited. Further, injection of the dye can cause local thrombophlebitis, though this is now rare with modern contrast agents.

Another approach used in assisting catheter guidance is endoscopy, a technique using a fiber optic camera to visualize the blood vessel interior. This method can be effective, but is expensive and is not always adaptable to the geometries required of a guiding catheter intended for applications such as right heart access.

There is a need for an improved guiding catheter for accessing heart vessels that can be easily guided by a clinician through a convoluted pathway. There is a further need for a catheter that provides an inexpensive and safe way to visualize the location of the catheter tip relative to an opening of a destination vessel during a cannulation procedure. The present invention fulfills these and other needs, and addresses other deficiencies of prior art implementations and techniques.

SUMMARY OF THE INVENTION

To overcome the limitations in the prior art described above, and to overcome other limitations that will become apparent upon reading and understanding the present specification, the present invention discloses a steerable guiding catheter that can provide access to venous structures for medical procedures.

In one embodiment, a guiding catheter system includes a flexible shaft having an open lumen and a pre-shaped distal bend. An ultrasonic transducer is supported by the flexible shaft proximal to the pre-shaped distal bend. A field of view of the ultrasonic transducer substantially encompasses at least a distal tip of the flexible shaft. A conductor is coupled to the ultrasonic transducer. The conductor is disposed along the flexible shaft.

The guiding catheter may further include an inner guiding catheter movably disposed within the open lumen of the flexible shaft. The ultrasonic transducer may include a one-dimensional array, two-dimensional array, and/or a pulsed Doppler transducer. The ultrasonic transducer can be mounted to substantially encompass a partial circumferential portion of the flexible shaft. The partial circumferential portion in this configuration faces towards the distal tip of the flexible shaft. In another configuration, the ultrasonic transducer comprises a substantially planar piezoelectric crystal and a plastic lens.

In one arrangement, the flexible shaft further includes at least one pull wire slidably disposed within the open lumen. The pull wire is fixably attached at a distal location of the flexible shaft. A tensile force applied to the pull wire causes a deflection of the distal tip of the flexible shaft.

In another embodiment, a guiding catheter system includes a flexible shaft comprising a guide lumen, a sensor lumen and a pre-shaped distal bend. The sensor lumen has a distal opening on the flexible shaft proximate the pre-shaped distal bend. The distal opening of the sensor lumen can be on an inner and/or outer surface of the flexible shaft. The catheter includes a sensor member having an elongated shaft, an ultrasonic transducer at a distal end of the elongated shaft, and a conductor coupled to the ultrasonic transducer and disposed along the elongated shaft. The sensor member is movably disposed within the sensor lumen of the flexible shaft. A distal tip of the sensor member is displaceable with respect to the distal opening of the sensor lumen allowing a field of view of the ultrasonic transducer to substantially encompass at least a distal tip of the flexible shaft. In one arrangement, the guiding catheter further includes an inner guiding catheter movably disposed within the guide lumen of the flexible shaft.

In another embodiment, a method of cannulating a destination vessel involves introducing a flexible shaft into an access vessel. The flexible shaft includes a pre-shaped distal end and an ultrasonic sensor proximal to the pre-shaped distal end, a field of view of the ultrasonic transducer to substantially encompassing at least a distal tip of the flexible shaft. The flexible shaft is distally advanced towards the destination vessel. Signals are read from the ultrasonic transducer to locate the destination vessel as the distal tip of the flexible shaft nears the destination vessel. The destination vessel is cannulated with the distal tip of the flexible shaft. The method may further involve introducing a payload through the flexible shaft. The method may also involve steering the flexible shaft.

In one particular approach, the ultrasonic transducer is extended distally through a wall of the flexible shaft. The destination vessel is located using the ultrasonic transducer signals from the ultrasonic transducer while extended. After locating the destination vessel, the flexible shaft is advanced toward the ultrasonic transducer until the field of view of the ultrasonic transducer substantially encompasses at least the distal tip of the flexible shaft.

According to another aspect of the method, the ultrasonic transducer is mounted to a Wire. The wire is advanced to extend the ultrasonic transducer distally of the flexible shaft. After locating the destination vessel, the flexible shaft is advanced over the wire until the field of view of the ultrasonic transducer substantially encompasses at least the distal tip of the flexible shaft.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 2 is a side view of a distal end of the catheter according to an embodiment of the present invention;

FIG. 3 is a cross sectional view of the catheter of FIG. 2, corresponding to section 1-1;

FIG. 4A is a cross sectional view of the catheter shaft corresponding to section 2-2 of FIG. 2 showing an ultrasonic sensor;

FIG. 4B is a cross sectional view of the catheter shaft corresponding to section 2-2 of FIG. 2 showing an alternate ultrasonic sensor configuration;

Figure 1:
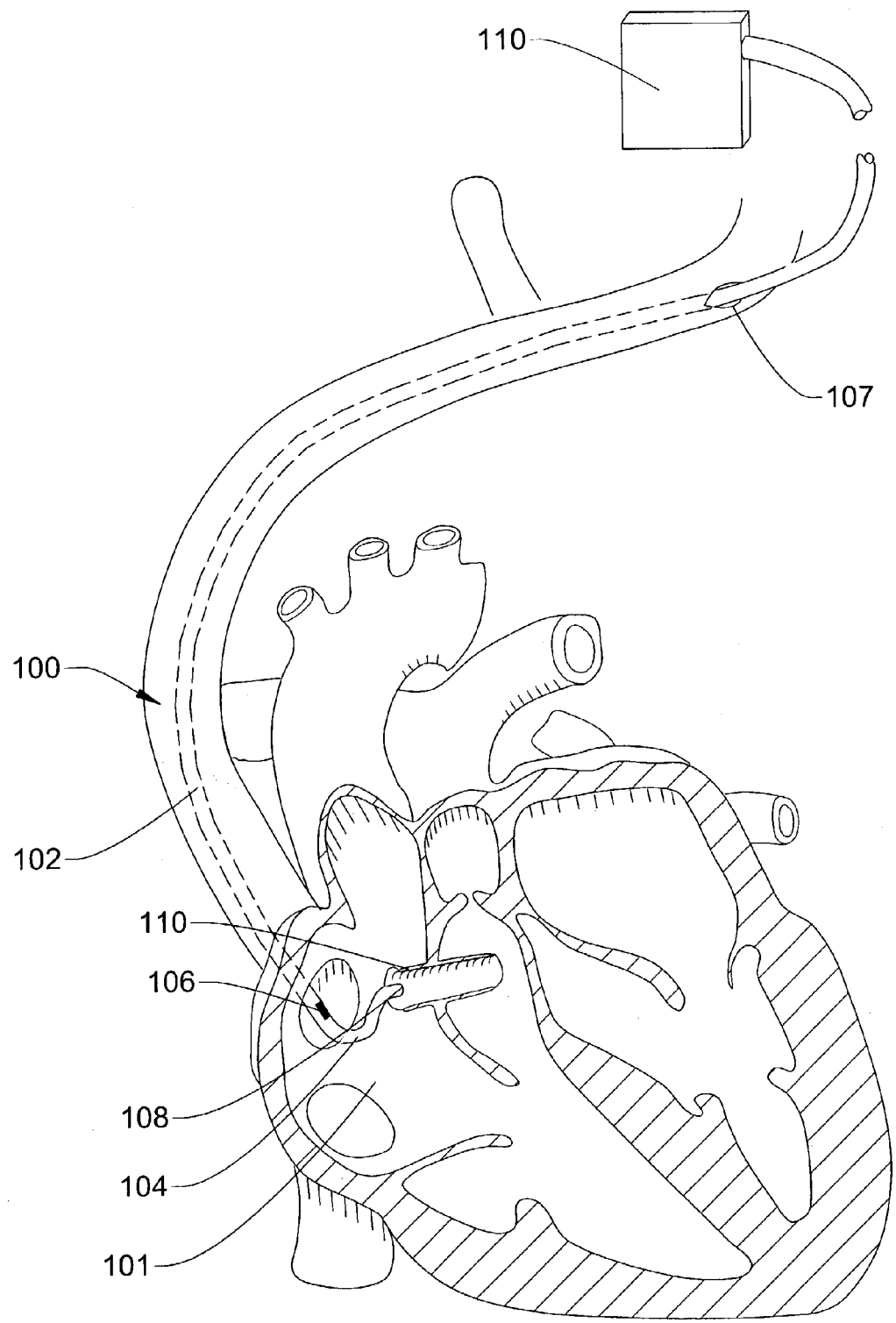
FIG. 1 is a cutaway view of a heart, showing a guiding catheter according to an embodiment of the present invention deployed in the right atrium.

While the invention is amenable to various modifications and alternative forms, specifics thereof have been shown by way of example in the drawings and will be described in detail herein. It is to be understood, however, that the intention is not to limit the invention to the-particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a guiding catheter system of the present invention employs a flexible shaft having a pre-formed bend at a distal end. An ultrasound transducer is mounted proximal to the pre-formed bend. The ultrasound transducer has a field of view directed to a distal tip of the guiding catheter. The guiding catheter includes an open lumen adapted for the introduction of payloads through the catheter system. The guiding catheter system can be used to direct a smaller guiding catheter or guide wire into a destination vessel from a heart chamber. In one application, the guiding catheter system is used to introduce a guiding catheter into the coronary sinus ostium from the right atrium.

Turning now to FIG. 1, a guiding catheter, generally indicated by reference numeral 100, is shown deployed in the right atrium 101 of the heart. The guiding catheter 100 includes a flexible shaft 102, a pre-shaped distal end 104, and an ultrasonic sensor 106. The ultrasonic sensor 106 is positioned proximal of the pre-shaped distal end 104. This location advantageously provides the ultrasonic sensor 106 a location from where it can view a distal tip 108 of the guiding catheter 100 during a cannulation procedure. The ultrasonic sensor 106 operates according to principles well known in the art, namely the transmittal and reflection of high frequency sound waves. The ultrasonic signals are transmitted to and from a proximal device 110 that is coupled to the ultrasonic sensor 106. The proximal device 110 is used for at least processing sensor readings. The proximal device 110 may include a display or, alternatively, may communicate processed sensor signals to a peripheral display coupled to the proximal device 110.

During a cannulation procedure, the guiding catheter 100 is inserted into an access vessel through an incision or introducer sheath puncture 107. The access vessel may include any of the large veins of the upper limb system such as the cephalic or subclavian veins. Lower limb vessels such as the femoral artery are also used as access points for many heart cannulation procedures. While the catheter 100 is being inserted through the large access vessel, the pathway is relatively uncomplicated and the guiding catheter 100 only requires a distally directed axial force to advance along the pathway. However, when a major branch vessel or a large cavity (e.g., a heart chamber) is reached, some degree of manipulation of the catheter 100 is required to guide the distal tip 108 in the desired direction. Additionally, the physician may inject radiopaque contrast media through the catheter 100 to aid in locating such features as the wall of the atrium 101 or flow out of the coronary sinus 110.

Although reaching the heart chamber itself is not unduly challenging, attempting to access another vessel, such as the coronary sinus 110 from the right atrium 101, is more difficult. This difficulty arises because the right atrium 101 is much larger relative to the size of the vessel pathway of interest. Moreover, the location of the coronary sinus 110 varies in patients, particularly patients with diseased hearts. A typical prior art approach to locating a vessel of interest involves use of contrast mapping (fluoroscopy) in concert with a radio-opaque pre-shaped catheter. The physician manipulates a proximal end of the catheter while watching the movements at the catheter's distal end on an X-ray display.

As an alternative to fluoroscopy, an ultrasonic sensor 106 according to the present invention provides visual cues to the clinician for locating the destination vessel, thereby eliminating the need to use potentially deleterious X-ray mapping procedures. This use of ultrasound is advantageous in at least avoiding the prolonged exposure to harmful X-rays. Further, the visualization offered by the sensor's mounting location provides a field of view that can be directed to a particular area of interest, namely the distal tip 108 of the catheter 100. This sensor view remains fairly constant even with continuous adjustment of the catheter's orientation in space, thereby providing a continuous sectional view of the catheter tip 108 and cardiac structures adjacent to the catheter tip 108.

Another advantage in using an ultrasonic sensor over X-ray fluoroscopy involves image quality. Fluoroscopy has poor image contrast when revealing cardiac structures in comparison to ultrasound. Also, because the shape of images revealed by fluoroscopy are highly dependent on the incident angles of the incoming X-rays, image distortion may result without constant adjustment of the incident angle. In contrast, a catheter 100 according to the present invention avoids distortions because the view angle of the sensor 106 is fixed relative to the flexible shaft 102.

Locating the ultrasonic sensor 106 proximal to the distal bend 104 provides other benefits. For example, the sensor 106 requires a number of electrical conductors to carry signals to and from the proximal end of the flexible shaft 102 to processing device 110. These conductors have the effect of stiffening the catheter 100. The sensor 106 often includes a piezoelectric crystal, and is therefore rigid. Situating the sensor 106 proximal to the pre-formed curve 104 advantageously allows the distal end of the catheter 100, including the pre-formed curve 104, to remain flexible. Having a flexible distal end is a distinct advantage when navigating the catheter 100 through a convoluted guide path. A more flexible preformed distal end 104 will have lower bending resistance as it is straightened for maneuvering through the guide path. A lower bending resistance decreases the probability of the catheter 100 abrading or perforating tissue along the guide path.

Turning now to FIG. 2, specifics of catheter 100 construction are illustrated. The pre-shaped distal end 104 has a shape that is optimized for a particular application, such as accessing the coronary sinus from the right atrium. The ultrasonic sensor 106 can include one or more piezoelectric crystals bonded to an inside or outside surface of the flexible shaft 102.

In this application, using an array of piezoelectric crystals is useful for providing a two- or three-dimensional image derived from the ultrasound readings. An array includes a number of small independent transducers in a one- or two-dimensional array. Each transducer in the array can be switched on and off at pre-set intervals and patterns. Some of the array transducers are activated at preset intervals and patterns to transmit an ultrasonic pulse, while others act as receivers of the resulting echoes. In some arrangements, a transmitting transducer may also act as a receiver of the echoes received from its own pulse, although that is not the usual case.

Continuously changing the transmitting and receiving assignments of the transducers within an array can be used to scan the image data collection area in a manner analogous to a mechanical scanner. Despite the necessary complexity of the array transducer and the associated software and circuitry required to form the scanned images, arrays offer advantages over mechanical scanning. A mechanical system requires the sensor to be rotated and/or translated in a controlled manner to form the image. Controlling such movement accurately near the distal tip of a catheter is difficult and even the best systems produce image with some distortions. An array requires no sensor movement and produces a reliably undistorted image. Additionally, mechanical systems require a lumen and mechanical clearance to accommodate the moving sensor and its mechanical linkages, which may require more space in the catheter than an array and its electrical conductors/optical fibers.

An array type sensor is much more reliable when it is supported in a manner that keeps it from flexing during use. In the layout of FIG. 2, the sensor 106 is placed proximate the curve(s) of the distal end 104. It is advantageous to place the sensor 106 proximate the curves because making this portion stiffer will not significantly reduce catheter maneuverability (as might be the case if the sensor 106 was mounted near the distal tip 108). Stiffening portions of the flexible shaft 102 to provide stability for the sensor 106 may be accomplished by adding a metallic stent-like structure or a metallic tube adjacent or encompassing the sensor 106. If metal reinforcing structures are added that surround the sensor 106, an aperture in the metal structure would be required so as to not obstruct the sensor's wavepath and field of view.

The sensor 106 requires a number of conductors 302 be provided along the flexible shaft 102, as seen in the cross sectional view of FIG. 3. The conductors 302 are loosely disposed through slightly oversized lumens 303 in the walls of the flexible shaft. Distributing the conductors 302 around the shaft 102 in oversized lumens 303 allows the shaft 102 to flex without placing large forces on the conductors 302. Although the conductors 302 are typically electrical conductors (e.g. copper wires), other signal transmission media such as optic fiber may also be included with the conductors 302.

The conductors 302 are coupled to the sensor 106, as seen in FIG. 4A. The sensor 106 in this arrangement is a generally curved array of transducers conforming to the walls of the flexible shaft 102. The sensor 106 is shown attached to an inner surface of the flexible shaft 102. In this arrangement, a protective layer 402 may be desired to protect the sensor 106 from items introduced through the flexible shaft 102. FIG. 4B shows an alternate arrangement, where the sensor 106 is embedded between the lining 304 and an outer casing 408 of the flexible shaft 102.

The curved sensor 106 shown in FIGS. 4A and 4B may be formed by partially wrapping side by side piezoelectric transducers in a line around the shaft to form at least one one-dimensional array. This arrangement produces a 2-D image shaped like a pie-slice. A two-dimensional array may also be formed by the appropriate arrangement of transducers.

Figure 4C:
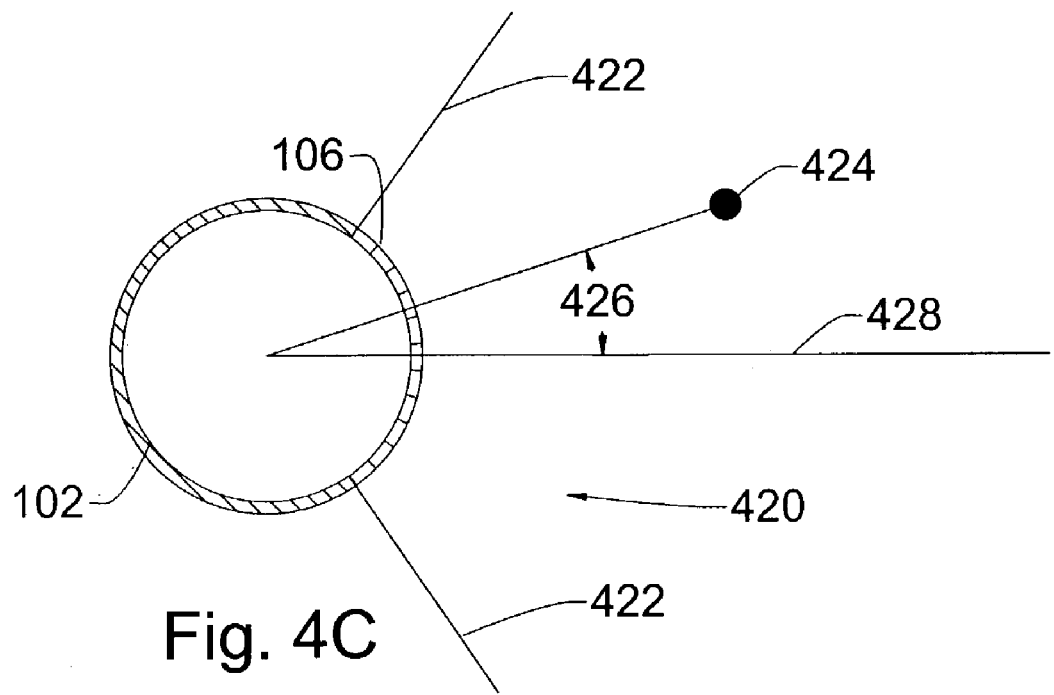
FIG. 4C is a diagram showing cross sectional viewing characteristics of an ultrasonic sensor according to the present invention.
Figure 4D:
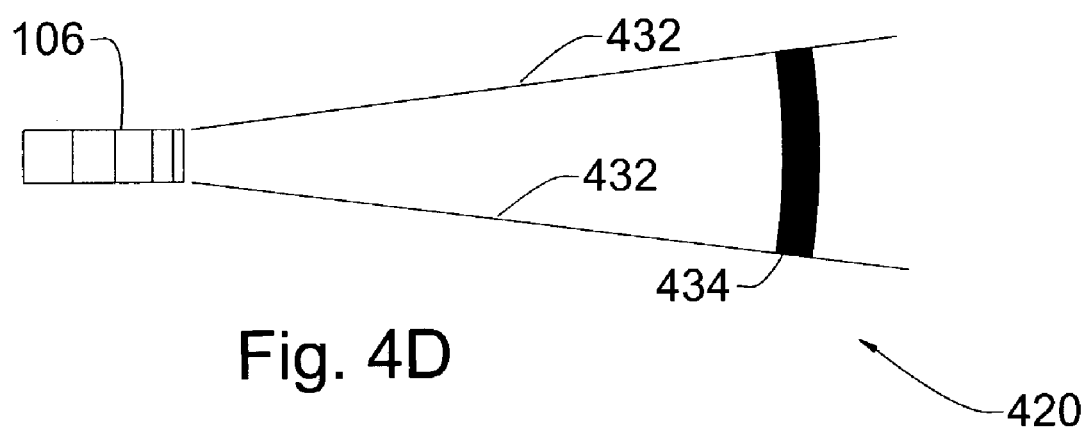
FIG. 4D is a diagram showing side viewing characteristics of an ultrasonic sensor according to the present invention.

FIGS. 4C and 4D illustrate the operation of a one-dimensional array sensor 106. The image appears as a slice shape originating at the sensor 106 and extending out through the catheter 100 and any cardiac structures in the path of the ultrasonic beam. At about 25 MHz or below, blood provides weak echoes and is therefore weakly imaged.

The displayed image represents a single pie-shaped slice with essentially no thickness. The echoes that create this image come from the region known as the beam path 420 that the ultrasonic pulses travel through. A width boundary 422 shown in FIG. 4C and a thickness boundary 432 shown in FIG. 4D define the edges of the boundary path 420. The beam path 420 gets wider as the pulse travels further from the sensor 106. As the sensor 106 "scans" across its width, the ultrasonic beams echo off a point 424. The point 424 is located at a planar angle 426 relative to an image centerline 428. The displayed image is formed by resolving multiple echoes across the beam path 420.

The image data from a single dimension array cannot be resolved to determine where in the thickness dimension (e.g., between boundary lines 432 in FIG. 4D) the echo is coming from. The displayed image at any point represents the intensity of the sum of all the echoes received at a planar angle and distance from the sensor, regardless of the position in the thickness dimension. Therefore, the area 434 will resolve as a single point, such as the point 424 shown in FIG. 4C.

By positioning the sensor 106 such that the distal tip 108 is partially in view of the sensor along the thickness boundary 432, both the tip 108 and structures adjacent the tip 108 will be in view. The position of tip 108 and other objects within the thickness boundary 432 can be resolved by using a two-dimensional array or more than one single dimensional array.

Just as the lines of varying depth of a one-dimensional array are assembled into a two-dimensional, slice-shaped image, the signals from a two-dimensional array can be resolved into a three-dimensional image. This three-dimensional image matrix can be displayed in a number of ways. Particularly useful is to display image slices across the width in a repeating sequence from down to up in the thickness dimension. Alternatively, image slices across the thickness can be shown in a repeating sequence from left to right across the width dimension. Either method would allow catheter motion direction and displacement to be easily visualized from changes in the displayed images.

Ultrasonic information derived from one- or two-dimensional sensor arrays may be analyzed for their content and thereby used to calculate Doppler shift. The Doppler shift can be color coded into the displayed image to indicate direction of motion. Also, the intensity of colors can be coded into the display to indicate the speed of motion. This can be particularly useful in locating the coronary sinus, as the venous blood will be flowing out of the sinus relative to the right atrium wall and, most likely, towards the ultrasonic sensor catheter 100.

Figure 5:
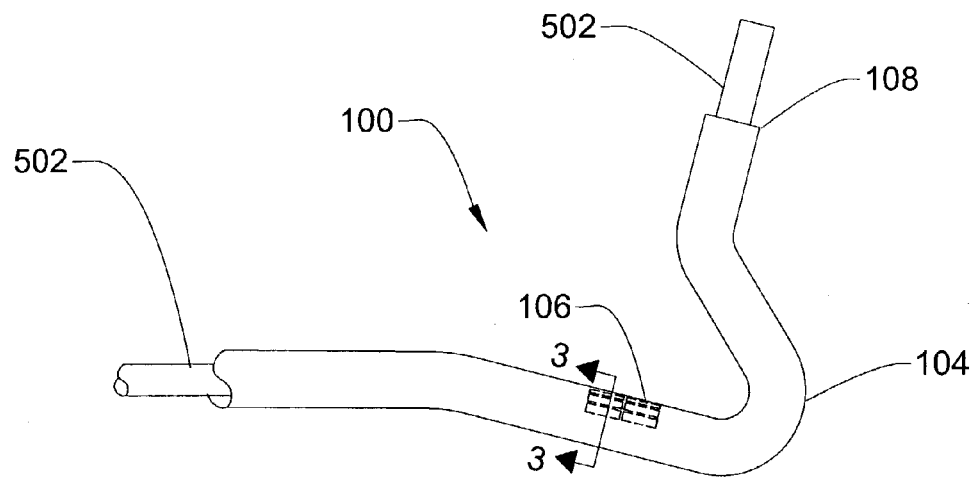
FIG. 5 is a side view of a distal end of a catheter embodying features according to the present invention.
Figure 6A:
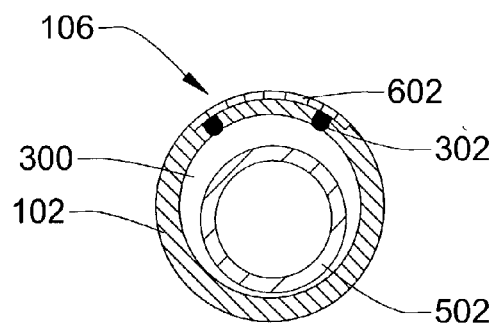
FIG. 6A is a cross sectional view of the catheter in FIG. 5, corresponding to section 3-3 showing a sensor arrangement according to the present invention.
Figure 6B:
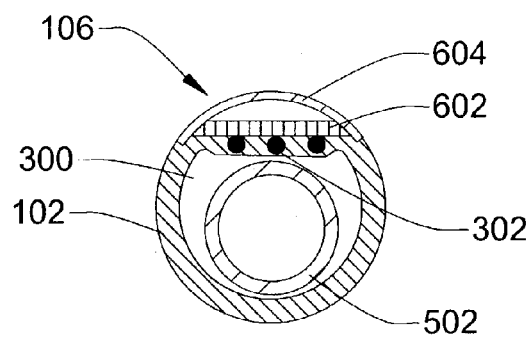
FIG. 6B is a cross sectional view corresponding to section 3-3 of FIG. 5 showing an alternate sensor arrangement according to the present invention.

There are other arrangements of an ultrasonic sensor 106 that can be used in accordance with the principles of the present invention. FIGS. 5, 6A, and 6B show an alternate arrangement of an ultrasonic sensor 106 on the flexible shaft 102. In FIG. 5, the catheter 100 includes a pre-shaped distal curve 104 having a different profile than that shown in FIG. 2. The ultrasonic sensor 106 in this configuration is located on a shaft surface facing towards the general direction of the distal tip 108. The sensor 106 can be a curved array mounted on an outer surface of the flexible shaft 102 as seen in FIG. 6A. In another arrangement, the sensor 106 includes one or more transducers 602 and a lens 604, as seen in FIG. 6B. The transducer 602 in this arrangement is substantially planar and located behind the plastic lens 604. In both arrangements, the orientation between the distal tip 108 and the sensor 106 remains within a predictable range of deflection of the pre-formed distal end 104. Therefore, the sensor 106 can be designed to focus within a predetermined space corresponding to the deflection range of the pre-formed distal end 104.

Referring again to FIG. 6B, the lens 604 encompasses the planar face of the transducer 602, keeping the outer shaft profile smooth as well as providing focusing of ultrasonic waves. The lens 602 works by delaying portions of the wavefront generated by the transducer 602. When the transducer 602 is configured as an arrayed system, electronic focusing can also be used. An array can achieve a focusing effect electronically by further modifying the pulsing sequence to create predetermined delays in selected elements within the phased array.

Due to the focusing of the sensor 106 with respect to the distal tip 108, the pre-formed distal end 104 is generally designed to maintain a constant shape when deployed within a heart chamber or other large cavity. This constant shape may be useful for general purposes, but is not always adaptable to varying anatomy or diseased tissue structures. A useful adaptation that allows to the present invention to more adaptively change distal geometry includes deploying an inner guiding catheter 502 within the open lumen 300 of the flexible shaft 102.

The inner guiding catheter 502, best seen in FIGS. 5, 6A, and 6B, can be slidably deployed within the open lumen 300 and is extendable beyond the distal tip 104 of the flexible shaft 102. Besides providing an effective length extension to the catheter 100, the guiding catheter 502 is smaller than the flexible shaft 102 and may be more suited for cannulating a smaller vessel such as the coronary sinus. In such an application, the pre-formed distal end 104 of the flexible shaft 102 provides a visually locatable staging point, and the inner guiding catheter 502 can be advanced beyond the staging point for further probing and then be deep-seated into the destination vessel.

Figure 7A:
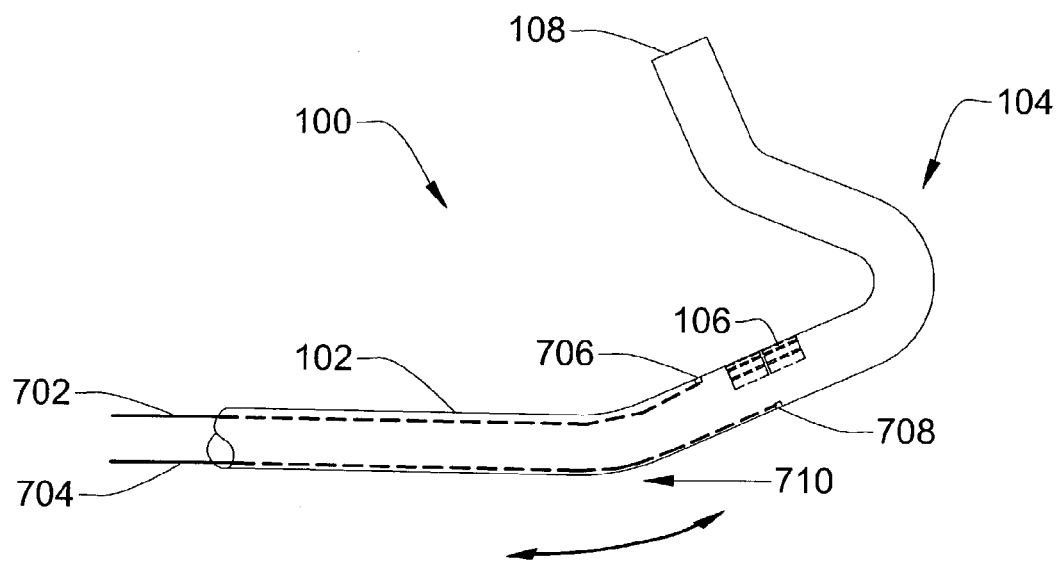
FIG. 7A is a side view of a catheter of the present invention employing one or more pull wires for steering the catheter.
Figure 7B:
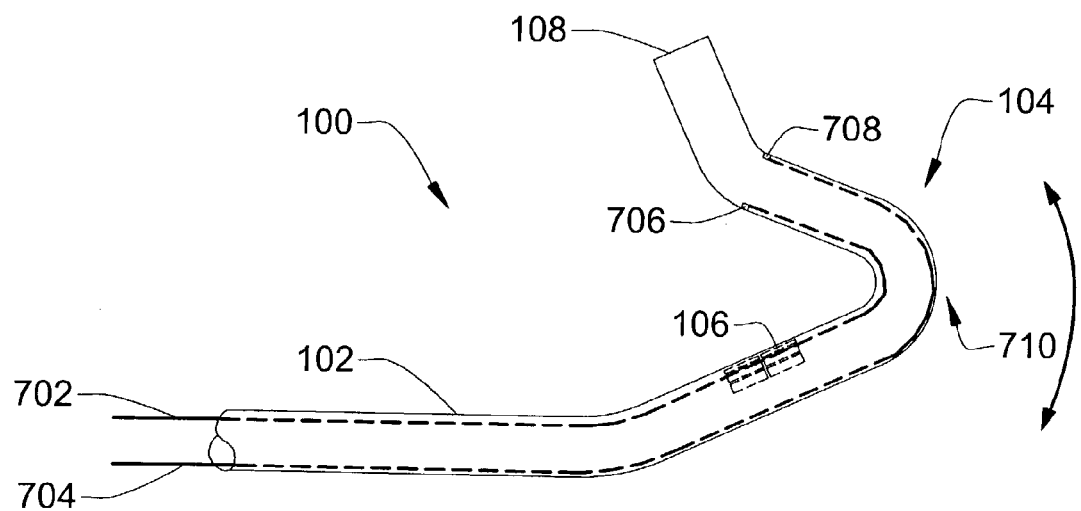
FIG. 7B is a side view of a catheter of the present invention employing one or more pull wires for steering the catheter with an alternate deflection point.

Another enhancement to a catheter according to the present invention includes deploying one or more pull wires 702, 704 as illustrated in FIGS. 7A and 7B. The pull wires 702, 704 are affixed at one end to attachment points 706, 708. In this configuration, pulling on wires 702, 704 separately causes the distal end to rotate about a deflection point 710. The pre-shaped distal end 104 moves around the deflection point 710 in the directions indicated by the curved arrows. In FIG. 7A, the deflection point is proximate the preformed distal end 104 so that the entire end 104 deflects. In FIG. 7B, the deflection point 710 is nearer the distal tip 108, so that only a small portion of the shaft 102 near the tip is deflected. The deflection point 710 usually includes a localized section of lowered flexural modulus, thereby allowing the shaft 102 to bend only near the deflection point 710. The pull wires 702,704 may be deployed through separate lumens (not shown), or otherwise slidably restrained to the walls of the flexible shaft 102. The pull wires 702, 704 may be coated with a lubricous material (e.g. Teflon). Additionally, any lumens or other structures containing the pull wires 702, 704 can have an inner lubricious lining.

Utilization of pull wires 702, 704 allows a clinician additional maneuverability when attempting to locate and/or cannulate a vessel with the catheter 100. It is appreciated that the location of the deflection point 710 is preferably proximal to the ultrasonic sensor 106. This advantageously keeps the orientation between the sensor 106 and distal tip 108 relatively constant while pull wires 702, 704 are being used. In this way, the sensor 106 provides a field of view directed towards the distal tip 108 even while the distal tip 108 is being deflected.

Figure 8A:
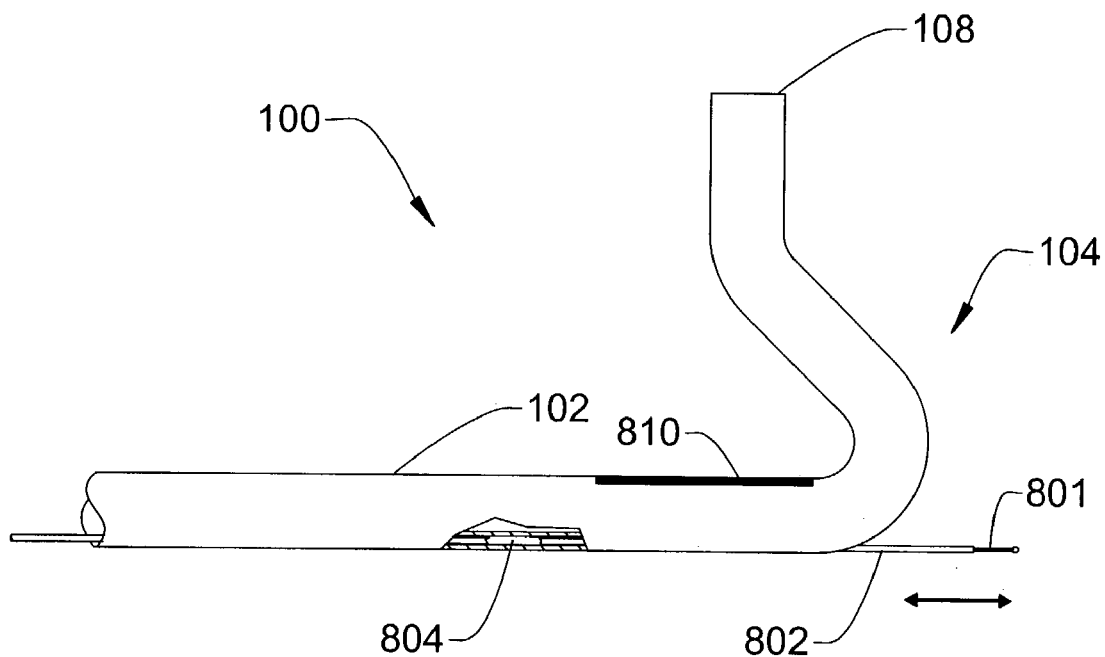
FIG. 8A is a side view of the distal end of a catheter showing another sensor arrangement according to an embodiment of the present invention.
Figure 8B:
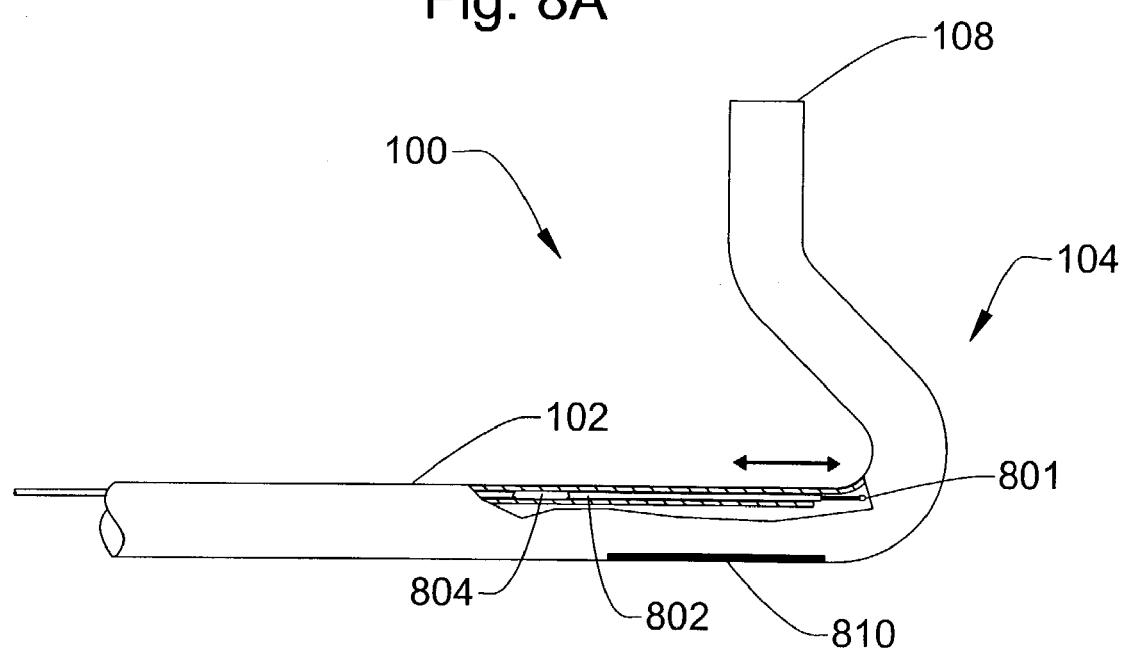
FIG. 8B is a side view of the distal end of a catheter showing an alternate sensor arrangement according to an embodiment of the present invention.

An alternative embodiment of the guiding catheter 100 is shown in FIGS. 8A and 8B. An ultrasonic sensor 801 is mounted on an elongated shaft 802, typically a flexible wire or other small diameter, elongated member such as used in an intravascular ultrasound (IVUS) catheter. The shaft and sensor 802, 801 can be designed similar to a conventional imaging core of a mechanical IVUS catheter or be made as a single transducer guidewire.

The elongated shaft 802 is movably disposed within a sensor lumen 804 provided in or on the flexible shaft 102. The elongated shaft 802 is rotated to mechanically scan an ultrasonic image at the sensor 801. As shown in the arrangement of FIG. 8A, a distal tip of the elongated shaft 802 is extendable beyond the sensor lumen 804 such that the sensor 801 can protrude outside the flexible shaft 102. The double-sided arrow indicates the directions the elongated shaft 802 can be adjusted. This allows the sensor 801 to view an area past the catheters distal end 104.

Another arrangement of a shaft-mounted sensor is shown in FIG. 8B. In this arrangement, the elongated shaft 802 is located in a sensor lumen 804 on a side of the flexible shaft 102 nearest the distal tip 108. Although the sensor 801 in this arrangement cannot extend past the distal end 104 of the catheter, the internal location allows the shaft and sensor 802, 801 to be rotated and translated without worries of damaging cardiac structures or becoming damaged at an exit point from the sensor lumen 804. Although FIGS. 8A and 8B show two example locations of the sensor lumen 804 and elongated shaft 802, it is appreciated that the sensor lumen 804 and elongated shaft 802 can be located on any location on the outer periphery of the flexible shaft 102.

Although the small sensor 801 may have a reduced field of view as compared to a fixed sensor mounted to the flexible shaft 102, this implementation has the advantage of being adjustably locatable, and independently moveable, relative to the flexible shaft 102. Adjustably locating the sensor 801 provides a modifiable ultrasonic field of view during cannulation proceedings.

In the embodiment illustrated in FIGS. 8A and 8B, the elongated shaft 802 preferably includes sensor conductors within the elongated shaft's body. As the sensor 801 in this embodiment is relatively small, constructing the sensor 801 from one or more linear arrayed piezoelectric crystal transducers is a typical approach. Pulsed and/or continuous ultrasound modes could be utilized with a sensor 801 of this configuration.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guiding catheter system, comprising:
   a flexible shaft comprising an open lumen and a pre-shaped distal bend;
   an ultrasonic transducer supported by the flexible shaft proximal to the pre-shaped distal bend, a field of view of the ultrasonic transducer substantially encompassing at least a distal tip section of the flexible shaft and a path of an ultrasonic signal emitted from the ultrasonic transducer being generally parallel with a longitudinal axis of the distal tip section when the distal bend pre-shape is assumed; and
   at least one conductor coupled to the ultrasonic transducer, the at least one conductor disposed along the flexible shaft.

2. The system of claim 1, further comprising an inner guiding catheter movably disposed within the open lumen of the flexible shaft.

3. The system of claim 1, wherein the ultrasonic transducer comprises an array of transducers.

4. The system of claim 3, wherein the array of transducers is a one-dimensional array.

5. The system of claim 3, wherein the array of transducers is a two-dimensional array.

6. The system of claim 1, wherein the ultrasonic transducer comprises one or more piezoelectric crystals.

7. The system of claim 1, wherein the ultrasonic transducer further comprises a pulsed Doppler transducer.

8. The system of claim 1, wherein the ultrasonic transducer is mounted to encompass a partial circumferential portion of the flexible shaft, the partial circumferential portion facing towards the distal tip of the flexible shaft.

9. The system of claim 1, wherein the ultrasonic transducer comprises a substantially planar piezoelectric crystal and a plastic lens.

10. The system of claim 1, wherein the flexible shaft further comprises at least one pull wire slidably disposed within the open lumen, the at least one pull wire fixably attached at a distal location of the flexible shaft, a tensile force applied to the at least one pull wire causing a deflection of the distal tip of the flexible shaft.

11. The system of claim 10, wherein the at least one pull wire is fixably attached proximal to the ultrasonic transducer.

12. A guiding catheter system, comprising:
    a flexible shaft comprising a guide lumen, a sensor lumen and a pre-shaped distal bend, the sensor lumen having a distal opening on the flexible shaft proximate the pre-shaped distal bend; and
    a sensor member, comprising:
      an elongated shaft when the distal bend pre-shape is assumed;
      an ultrasonic transducer provided at a distal end of the elongated shaft; and
      at least one conductor coupled to the ultrasonic transducer and disposed along the elongated shaft;
      the sensor member movably disposed within the sensor lumen of the flexible shaft, a distal tip of the sensor member displaceable with respect to the distal opening of the sensor lumen allowing a field of view of the ultrasonic transducer to substantially encompass at least a distal tip of the flexible shaft.

13. The system of claim 12, wherein the distal opening of the sensor lumen is on an inner surface of the flexible shaft.

14. The system of claim 12, wherein the distal opening of the sensor lumen is on an outer surface of the flexible shaft.

15. The system of claim 12, wherein movement of the sensor member within the sensor lumen is controllable independent of movement of the flexible shaft.

16. The system of claim 12, further comprising an inner guiding catheter movably disposed within the guide lumen of the flexible shaft.

17. The system of claim 12, wherein the flexible shaft further comprises at least one pull wire slidably disposed within the open lumen, the at least one pull wire fixably attached at a distal location of the flexible shaft, a tensile force applied to the at least one pull wire causing a deflection of the distal tip of the flexible shaft.

18. The system of claim 12, wherein the ultrasonic transducer comprises one or more piezoelectric transducers.

19. A method of cannulating a destination vessel, comprising:
   introducing a flexible shaft into an access vessel, the flexible shaft comprising a pre-shaped distal end and an ultrasonic transducer proximal to the pre-shaped distal end, a field of view of the ultrasonic transducer substantially encompassing at least a distal tip of the flexible shaft when the distal bend pre-shape is assumed;
   distally advancing the flexible shaft towards the destination vessel;
   reading signals from the ultrasonic transducer to locate the destination vessel as the distal tip of the flexible shaft nears the destination vessel; and
   cannulating the destination vessel with the distal tip of the flexible shaft.

20. The method of claim 19, further comprising introducing a payload through the flexible shaft.

21. The method of claim 19, further comprising steering the distal tip of the flexible shaft.

22. The method of claim 19, further comprising:
   extending the ultrasonic transducer distally out of an opening in the wall of the flexible shaft; and
   locating the destination vessel using the ultrasonic transducer signals from the ultrasonic transducer while extending the ultrasonic transducer.

* * * * *